United States Patent
Hirt et al.

(10) Patent No.: US 10,702,286 B2
(45) Date of Patent: Jul. 7, 2020

(54) MEDICAL INSTRUMENTARIUM

(71) Applicant: Aesculap AG, Tuttlingen (DE)

(72) Inventors: Martin Hirt, Stockach (DE); Thomas Güttler, Tübingen-Hirschau (DE); Christian Bader, Hüfingen (DE)

(73) Assignee: Aesculap AG, Tuttlingen (DE)

( * ) Notice: Subject to any disclaimer, the term of this patent is extended or adjusted under 35 U.S.C. 154(b) by 206 days.

(21) Appl. No.: 16/016,834

(22) Filed: Jun. 25, 2018

(65) Prior Publication Data

US 2018/0303495 A1 Oct. 25, 2018

Related U.S. Application Data (63) Continuation of application No. PCT/EP2017/050450, filed on Jan. 11, 2017.

(30) Foreign Application Priority Data

Jan. 11, 2016 (DE) .................. 10 2016 100 312

(51) Int. Cl.
*A61B 17/16* (2006.01)

(52) U.S. Cl.
CPC ...... *A61B 17/1659* (2013.01); *A61B 17/1662* (2013.01); *A61B 17/1668* (2013.01)

(58) Field of Classification Search
CPC ............ A61B 17/1659; A61B 17/1662; A61B 17/1668
See application file for complete search history.

(56) References Cited

U.S. PATENT DOCUMENTS

| | | | |
|---|---|---|---|
| 4,552,136 A * | 11/1985 | Kenna | A61B 17/1659 606/85 |
| 5,041,118 A * | 8/1991 | Wasilewski | A61B 17/1659 606/85 |
| 5,993,455 A | 11/1999 | Noble | |
| 8,454,611 B2 | 6/2013 | Wallstein et al. | |
| 2007/0225821 A1 | 9/2007 | Reubelt et al. | |
| 2010/0023014 A1* | 1/2010 | Romagnoli | A61B 17/1659 606/85 |
| 2011/0160733 A1 | 6/2011 | Wallstein et al. | |
| 2012/0265319 A1* | 10/2012 | Prybyla | A61F 2/36 623/22.36 |

FOREIGN PATENT DOCUMENTS

| | | |
|---|---|---|
| AT | 34519 | 5/1985 |
| DE | 102008020192 | 10/2009 |
| DE | 102008020199 | 10/2009 |
| DE | 202010000184 | 7/2010 |
| EP | 0139520 | 5/1985 |
| WO | 9003794 | 4/1990 |

* cited by examiner

*Primary Examiner* — Christian A Sevilla
(74) *Attorney, Agent, or Firm* — Lipsitz & McAllister, LLC (57) ABSTRACT

The invention relates to a medical instrumentarium, in particular for implanting a hip joint stem, comprising a rasp instrument with a rasp shank defining a longitudinal axis, which rasp shank has an anterior side face, a posterior side face, a medial side face, and a lateral side face, wherein the side faces at least partially have rasp teeth which are formed running parallel to each other and circumferential or at least partially circumferential with respect to the longitudinal axis, wherein the rasp instrument comprises a rotational stabilization device for increasing a rotational stability of the rasp shank driven into a bone cavity, in particular a femur cavity.

17 Claims, 5 Drawing Sheets

MEDICAL INSTRUMENTARIUM

CROSS-REFERENCE TO RELATED APPLICATIONS

This application is a continuation of international application number PCT/EP2017/050450 filed on Jan. 11, 2017 and claims the benefit of German application number 10 2016 100 312.3 filed on Jan. 11, 2016, which are incorporated herein by reference in their entirety and for all purposes.

FIELD OF THE INVENTION

The present invention relates to medical instrumentaria generally, and more specifically to a medical instrumentarium, in particular for implanting a hip joint stem, comprising a rasp instrument which has a rasp shank defining a longitudinal axis, which rasp shank has an anterior side face, a posterior side face, a medial side face, and a lateral side face, wherein the side faces at least partially have rasp teeth which are formed running parallel to each other and circumferential or at least partially circumferential with respect to the longitudinal axis.

BACKGROUND OF THE INVENTION

Medical instrumentaria of the kind described hereinabove are known in many ways. In particular femur cavities into which a hip joint stem of a hip joint endoprosthesis is to be inserted are prepared with rasp instruments comprised by such medical instrumentaria. A surgeon begins in the preparation of the femur cavity with the smallest available rasp shank and drives this into the femur cavity. Then, the rasp shank is again removed from the femur cavity and a somewhat larger rasp shank is driven in. This procedure is repeated until the proper size of the rasp shank is determined.

Numerous surgeons use the largest rasp shank driven in to test rotational stability thereof in the femur. This is supposed to simulate rotational stability for example of a hip joint stem to ultimately be implanted.

A rasp shank with a toothing that is formed by the rasp teeth described at the outset which are formed circumferential or at least partially circumferential on the side faces of the rasp shank has been shown in tests to be not particularly well suited with respect to determine the rotational stability.

It is therefore the object of the present invention to improve a handling of a medical instrumentarium of the kind described at the outset, in particular in the preparation of a bone cavity, in particular a femur cavity.

SUMMARY OF THE INVENTION

In a first aspect of the invention, a medical instrumentarium, in particular for implanting a hip joint stem, which instrumentarium comprises a rasp instrument with a rasp shank defining a longitudinal axis. Said rasp shank has an anterior side face, a posterior side face, a medial side face, and a lateral side face. The side faces at least partially have rasp teeth which are formed running parallel to each other and circumferential or at least partially circumferential with respect to the longitudinal axis. The rasp instrument comprises a rotational stabilization device for increasing a rotational stability of the rasp shank driven into a bone cavity, in particular a femur cavity.

In a second aspect of the invention, a medical instrumentarium, in particular for implanting a hip joint stem, which instrumentarium comprises a rasp instrument with a rasp shank defining a longitudinal axis. Said rasp shank has an anterior side face, a posterior side face, a medial side face, and a lateral side face. The side faces at least partially have rasp teeth which are formed running parallel to each other and circumferential or at least partially circumferential with respect to the longitudinal axis. The rasp instrument comprises a rotational stabilization device for increasing a rotational stability of the rasp shank driven into a bone cavity, in particular a femur cavity. The rotational stabilization device comprises a multitude of stabilization grooves on at least one side face of the rasp shank and the multitude of stabilization grooves runs obliquely relative to the rasp teeth. The multitude of stabilization grooves at least partially has a U-shaped or V-shaped cross-sectional shape. A groove depth of the multitude of stabilization grooves on the lateral side face is greater than a tooth depth of the rasp teeth, and a groove depth of the multitude of stabilization grooves on the medial side face is less than a tooth depth of the rasp teeth.

In a third aspect of the invention, a medical instrumentarium, in particular for implanting a hip joint stem, which instrumentarium comprises a rasp instrument with a rasp shank defining a longitudinal axis. Said rasp shank has an anterior side face, a posterior side face, a medial side face, and a lateral side face. The side faces at least partially have rasp teeth which are formed running parallel to each other and circumferential or at least partially circumferential with respect to the longitudinal axis. The rasp instrument comprises a rotational stabilization device for increasing a rotational stability of the rasp shank driven into a bone cavity, in particular a femur cavity. The rotational stabilization device comprises a multitude of stabilization grooves on at least one side face of the rasp shank and the multitude of stabilization grooves runs obliquely relative to the rasp teeth. The medial side face has a proximal side face region and a distal side face region, and the proximal side face region is concavely curved pointing away from the rasp shank in a direction parallel to the longitudinal axis and is planar or convexly curved pointing away from the rasp shank in a direction perpendicular to the longitudinal axis. The multitude of stabilization grooves of the medial side face is formed in the proximal or substantially in the proximal side face region.

BRIEF DESCRIPTION OF THE DRAWINGS

The foregoing summary and the following description may be better understood in conjunction with the drawing figures, of which.

DETAILED DESCRIPTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a medical instrumentarium, in particular for implanting a hip joint stem, comprising a rasp instrument with a rasp shank defining a longitudinal axis, which rasp shank has an anterior side face, a posterior side face, a medial side face, and a lateral side face, wherein the side faces at least partially have rasp teeth which are formed running parallel to each other and circumferential or at least partially circumferential with respect to the longitudinal axis, wherein the rasp instrument comprises a rotational stabilization device for increasing a rotational stability of the rasp shank driven into a bone cavity, in particular a femur cavity.

The further development suggested according to the invention enables a surgeon to in particular test rotational stability with the rasp shank already driven into the bone cavity, for example the femur cavity, namely without having to insert the prosthesis stem to ultimately be implanted. Thus, the surgeon has the benefit of, on the one hand, preparing the bone cavity with the rasp instrument and determining the proper size of the shank implant to be implanted and, on the other hand, checking rotational stability of the implant stem in the bone with the rasp shank of the proper size driven in, namely with that rasp shank driven in which in this case forms a test implant, so to speak. An undesired rotation of the rasp shank in the bone cavity is minimized by the rotational stabilization device, such that a feeling of security in the doctor is increased with respect to the seating of the rasp shank in the bone cavity. A quantity of stabilization grooves per side face on which such stabilization grooves are provided is preferably greater than 6. In particular, up to 10 or even more stabilization grooves may be formed, in particular on the lateral and/or medial side face. A spacing of the stabilization grooves from each other is preferably maximally as large as a spacing of adjacent rasp teeth. The smaller the spacing, the greater a stability effect of the stabilization grooves running transversely.

It is favorable if the rotational stabilization device comprises a multitude of stabilization grooves on at least one side face of the rasp shank and if the multitude of stabilization grooves runs obliquely relative to the rasp teeth. A multitude of stabilization grooves may in particular be formed on the medial side face and/or the lateral side face. The stabilization grooves running obliquely may in particular entirely or partially prevent a rotation of the rasp shank driven into the bone cavity. In this way, rotational stability of the rasp shank driven into the bone cavity may be increased.

A particularly high rotational stability may in particular be achieved in that the multitude of stabilization grooves running obliquely relative to the rasp teeth run at a stabilization angle in a range from about 30° to about 60°. Favorably, the stabilization angle is in a range from about 40° about 50°. The stabilization angle is preferably 45°.

It is advantageous if the multitude of stabilization grooves is formed on the lateral side face and/or on the medial side face and/or on the anterior side face and/or on the posterior side face of the rasp shank. In particular, it is advantageous if the stabilization grooves are formed on the medial side face and on the lateral side face. For example, they may be formed or provided exclusively on these two side faces. In particular the medial side face and the lateral side face are in particularly large contact with the bone upon preparation of the bone cavity. Therefore, the formation of the multitude of stabilization grooves on the lateral side face and/or the medial side face is particularly advantageous for the improvement of the rotational stability.

In order to achieve in particular a rotational stabilization in mutually opposed directions of rotation, it is favorable if the multitude of stabilization grooves that are formed on the lateral side face and on the medial side face all run parallel or substantially parallel to each other. This means in particular that the stabilization grooves on the lateral side face as well as on the medial side face are tilted either toward the anterior or toward the posterior, but all stabilization grooves always in the same direction. In this way, a particularly high rotational stability may be achieved and namely independently of a direction of rotation.

Further, it may be advantageous if the multitude of stabilization grooves that are formed on the anterior side face and on the posterior side face all run parallel or substantially parallel to each other. This, too, means in turn that the stabilization grooves on the anterior side face as well as on the posterior side face run either obliquely toward the medial side face with respect to the longitudinal axis, namely on the anterior as well as on the posterior side face, or obliquely in the direction toward the lateral side face, namely on the anterior side face as well as on the posterior side face. Running substantially parallel to each other means here in particular that deviations of few degrees between an orientation of the stabilization grooves on the lateral side face running parallel to each other and the stabilization grooves on the medial side face running parallel to each other may be possible. Correspondingly, this also applies to the stabilization grooves on the anterior side face and on the posterior side face running substantially parallel to each other.

According to another preferred embodiment of the invention, provision may be made for proximal stabilization groove ends of the stabilization grooves formed on the lateral side face to be positioned closer to the posterior side face than to the anterior side face and for distal stabilization groove ends of the stabilization grooves formed on the lateral side face to be positioned closer to the anterior side face than to the posterior side face and for the proximal stabilization groove ends to be positioned further proximally with respect to the longitudinal axis than the distal stabilization groove ends. Such a configuration enables in particular forming stabilization grooves on the lateral side face in such a way that they run obliquely with respect to the longitudinal axis, namely obliquely in distal direction from the posterior side face in the direction pointing toward the anterior side face. By means of the configuration, a counterclockwise rotation of the rasp shank about the longitudinal axis in a view from proximal may be effectively stabilized.

For a stabilization of a clockwise rotation viewed from proximal, it is favorable if proximal stabilization groove ends of the stabilization grooves formed on the medial side face are positioned closer to the posterior side face than to the anterior side face and if distal stabilization groove ends of the stabilization grooves formed on the medial side face are positioned closer to the anterior side face than to the posterior side face and if the proximal stabilization groove ends are positioned further proximally with respect to the longitudinal axis than the distal stabilization groove ends. By means of this particular design of the stabilization grooves on the medial side face running obliquely, a rotational stabilization in a direction of rotation may be achieved that is oriented opposite to a rotation of the direction of rotation described above for the stabilization grooves on the lateral side face.

According to another preferred embodiment of the invention, provision may be made for proximal stabilization groove ends of the stabilization grooves formed on the anterior side face to be positioned closer to the lateral side face than to the medial side face and for distal stabilization groove ends of the stabilization grooves formed on the anterior side face to be positioned closer to the medial side face than to the lateral side face and for the proximal stabilization groove ends to be positioned further proximally with respect to the longitudinal axis than the distal stabilization groove ends. By means of this particular design of the stabilization grooves on the anterior side face, a counter-clockwise rotation about the longitudinal axis in top view from proximal onto the rasp shank may be stabilized.

For a rotational stabilization in the clockwise direction when viewing the rasp shank from proximal, it is advantageous if proximal stabilization groove ends of the stabilization grooves formed on the posterior side face are positioned closer to the lateral side face than to the medial side face and if distal stabilization groove ends of the stabilization grooves formed on the posterior side face are positioned closer to the medial side face than to the lateral side face and if the proximal stabilization groove ends are positioned further proximally with respect to the longitudinal axis than the distal stabilization groove ends.

The circumferential or substantially circumferential rasp teeth preferably each define a rasp tooth plane which runs transversely to the longitudinal axis. In particular, the rasp tooth plane may run perpendicularly to the longitudinal axis of the rasp shank. In particular then when the longitudinal axis of the rasp shank simultaneously defines a driving direction, the rasp teeth may particularly effectively rasp away bone material on inner faces of the bone cavity transversely to the driving direction.

A particularly good rotational stabilization may be achieved in particular in that the multitude of stabilization grooves at least partially has a U-shaped or V-shaped cross-sectional shape. A profile of the cross-sectional shape may be different depending on the respective side face of the rasp shank. The cross-sectional shape of all stabilization grooves on all side faces may be identical, however. This has in particular the advantage that the stabilization grooves may be formed in a simple manner with a single tool, for example by machining.

It is advantageous if the V-shaped cross-sectional shape defines a groove opening angle between groove side faces of a stabilization groove tilted relative to each other, which is in a range from about 30° to about 60°. In particular, the groove opening angle may be in a range from about 40° to about 50°. Forming V-shaped stabilization grooves in the defined way enables in particular achieving a particularly high rotational stability. Further, this particular design of the stabilization grooves prevents in particular that bone material in the interior of the bone cavity may be rasped away as a result of a rotation of the rasp shank about its longitudinal axis.

In particular for manufacturing the rasp shank, it is advantageous if the multitude of stabilization grooves has a chamfered groove base. Thus, stabilization grooves of the kind may be formed with a beveled cutter for example whose front end is rounded.

Favorably, a groove depth of the multitude of stabilization grooves on the lateral side face is greater than a tooth depth of the rasp teeth. A particularly good rotational stability may thus be achieved.

Furthermore, it may be advantageous if a groove depth of the multitude of stabilization grooves on the medial side face is less than a tooth depth of the rasp teeth. In this way, in particular unintended removal of bone material in the medial region may be avoided.

In order to minimize the removal of bone material in the bone cavity to the anterior and/or posterior, it is advantageous if a groove depth of the multitude of stabilization grooves on the anterior side face and/or on the posterior side face is less than a tooth depth of the rasp teeth.

According to another preferred embodiment of the invention, provision may be made for the medial side face to have a proximal side face region and a distal side face region and for the proximal side face region to be concavely curved pointing away from the rasp shank in a direction parallel to the longitudinal axis and to be planar or convexly curved pointing away from the rasp shank in a direction perpendicular to the longitudinal axis. Such a contour of the rasp shank enables an optimal adjustment of the bone cavity for accommodating a correspondingly curved prosthesis stem.

It is favorable if the multitude of stabilization grooves of the medial side face are formed in the proximal or substantially in the proximal side face region. A particularly good rotational stability, in particular in the proximal side face region, may thus be achieved, that is, there where the greatest torques must be transferred from the rasp shank to the bone.

Further, it may be favorable if the lateral side face has a proximal side face region and a distal side face region and if the proximal side face region is convexly curved pointing away from the rasp shank in a direction parallel to the longitudinal axis and is planar or convexly curved pointing away from the rasp shank in a direction perpendicular to the longitudinal axis. Such a configuration enables a particularly good adjustment of the contour of the bone cavity, in particular in the region of a trochanter major, upon preparation of a femur cavity with the rasp instrument.

Advantageously, the multitude of stabilization grooves of the lateral side face is formed in the proximal or substantially in the proximal side face region. A particularly good rotational stability may thus be achieved in particular in the region of the lateral side face, namely in the proximal side face region of the lateral side face.

In order to also improve rotational stability of the rasp shank in the direction toward a distal end of the rasp shank, it is advantageous if the multitude of stabilization grooves of the anterior side face and/or of the posterior side face are formed on the distal side of the proximal side face regions of the lateral side face and/or of the medial side face. In particular, spacings between adjacent stabilization grooves of the anterior side face and/or of the posterior side face may correspond to a multiple of a spacing of adjacent rasp teeth. In particular, a spacing of these stabilization grooves may be up to fivefold or even more of a spacing of adjacent rasp teeth.

It may be advantageous if the rasp teeth have a first rasp tooth side face running transversely or substantially transversely to the longitudinal axis and pointing in the distal direction and a second rasp tooth side face tilted with respect to the longitudinal axis and pointing substantially in proximal direction. With rasp teeth of that kind, a bone cavity may be enlarged in the desired way, in particular upon driving in the rasp shank.

A particularly good rasping effect may be achieved in particular in that the first and second rasp tooth side faces define between them a rasp tooth angle which is less than 90°. In particular, the rasp tooth angle may also be less than 70°.

For a further improvement of an effect of the rasp teeth, provision may be made in particular for the first rasp tooth side face to be tilted pointing somewhat in the direction toward the longitudinal axis for forming an undercut acting in the distal direction.

Further, it may be favorable if the rasp shank comprises a distal end section and if the distal end section of the rasp shank defines the longitudinal axis. Such a configuration is advantageous in particular then when a proximal end section of the rasp shank, which for example comprises the proximal side face regions defined above, does not run rectilinearly, but rather is formed curved.

A manufacturing of the instrumentarium, in particular the rasp instrument, may be simplified for example in that the anterior side face and/or the posterior side face and/or the lateral side face and/or the medial side face are formed at least partially planar or substantially planar. For example, the stated side faces may each individually or in any combination have planar face sections that run parallel to the longitudinal axis or instead are slightly tilted relative to the longitudinal axis. In particular, the distal side face regions of one or of all four side faces are formed planar or substantially planar.

It is favorable if a first coupling element is arranged or formed on the rasp shank in the region of its proximal end for detachably connecting to a rasp grip. This configuration enables in particular coupling the rasp shank to a rasp grip and driving the rasp shank into the bone cavity by striking the rasp grip. In order to in particular be able to consecutively drive multiple rasp shanks, for example of various sizes, into the bone cavity, the provision of the first coupling element enables the rasp shanks to each be able to be connected to the same rasp grip. In this way, a number of necessary parts of the instrumentarium for a surgical procedure may be reduced.

It is favorable if the rasp instrument is modularly formed and comprises a rasp grip that is detachably connectable to the rasp shank. As already described, the rasp grip may be formed in order to be able to connect it to various rasp shanks, in particular of various sizes.

The rasp grip preferably comprises a second coupling element which in a coupling position is engaged with the first coupling element and in a cleaning position is disengaged. By means of the second coupling element on the rasp grip, a unit may be simply formed in the shape of a rasp instrument, namely comprising a rasp shank and a rasp grip.

The present invention further relates to a medical instrumentarium, in particular for implanting a hip joint stem, comprising a rasp instrument with a rasp shank defining a longitudinal axis, which rasp shank has an anterior side face, a posterior side face, a medial side face, and a lateral side face, wherein the side faces at least partially have rasp teeth which are formed running parallel to each other and circumferential or at least partially circumferential with respect to the longitudinal axis, wherein the rasp instrument comprises a rotational stabilization device for increasing a rotational stability of the rasp shank driven into a bone cavity, in particular a femur cavity, wherein the rotational stabilization device comprises a multitude of stabilization grooves on at least one side face of the rasp shank and wherein the multitude of stabilization grooves runs obliquely relative to the rasp teeth, wherein the multitude of stabilization grooves at least partially has a U-shaped or V-shaped cross-sectional shape, wherein a groove depth of the multitude of stabilization grooves on the lateral side face is greater than a tooth depth of the rasp teeth, and wherein a groove depth of the multitude of stabilization grooves on the medial side face is less than a tooth depth of the rasp teeth.

The present invention further relates to a medical instrumentarium, in particular for implanting a hip joint stem, comprising a rasp instrument with a rasp shank defining a longitudinal axis, which rasp shank has an anterior side face, a posterior side face, a medial side face, and a lateral side face, wherein the side faces at least partially have rasp teeth which are formed running parallel to each other and circumferential or at least partially circumferential with respect to the longitudinal axis, wherein the rasp instrument comprises a rotational stabilization device for increasing a rotational stability of the rasp shank driven into a bone cavity, in particular a femur cavity, wherein the rotational stabilization device comprises a multitude of stabilization grooves on at least one side face of the rasp shank and wherein the multitude of stabilization grooves runs obliquely relative to the rasp teeth, wherein the medial side face has a proximal side face region and a distal side face region, and wherein the proximal side face region is concavely curved pointing away from the rasp shank in a direction parallel to the longitudinal axis and is planar or convexly curved pointing away from the rasp shank in a direction perpendicular to the longitudinal axis, and wherein the multitude of stabilization grooves of the medial side face is formed in the proximal or substantially in the proximal side face region.

Depicted in FIGS. 1 to 11 is for example a rasp instrument designated as a whole by the reference numeral 10 of a medical instrumentarium designated as a whole by the reference numeral 12.

Figure 2:
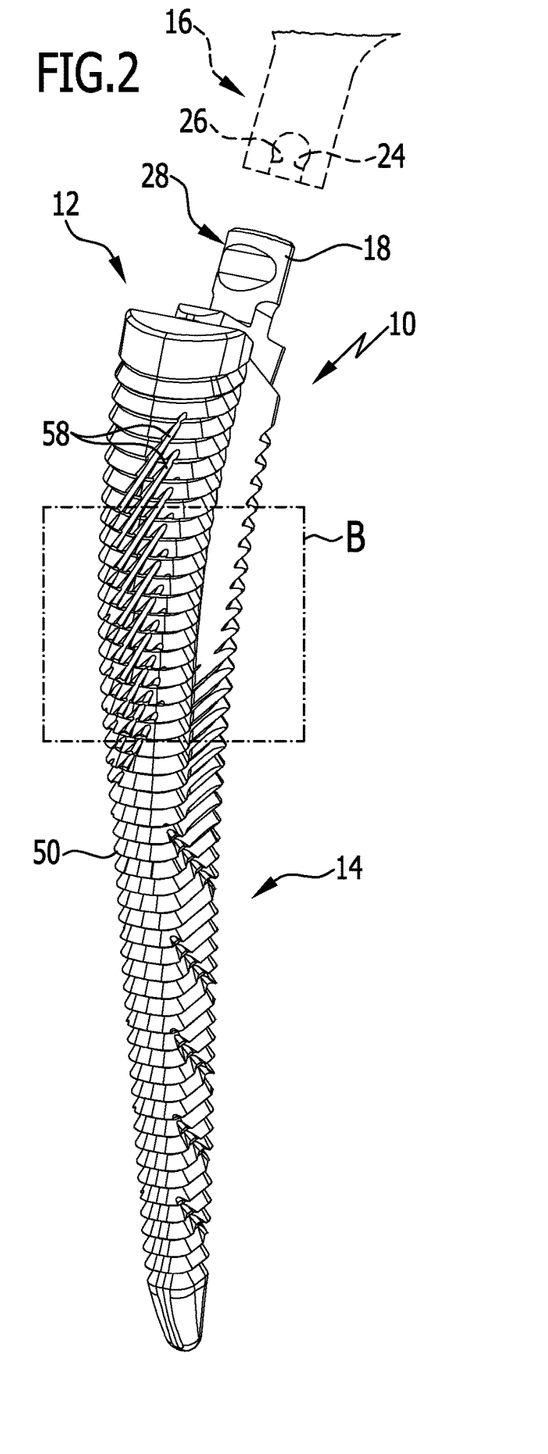
FIG. 2: shows a perspective view of the rasp shank from FIG. 1 in the direction toward its lateral side face and its posterior side face.
Figure 3:
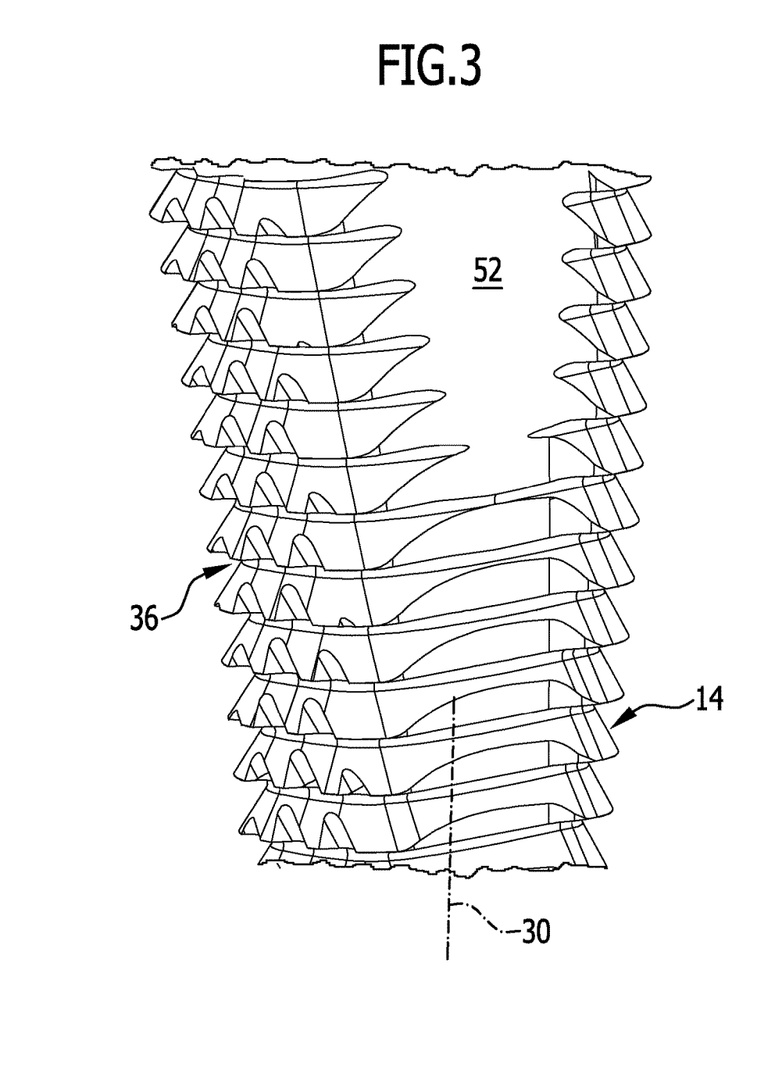
FIG. 3: shows an enlarged view of Region A in FIG. 1.
Figure 4:
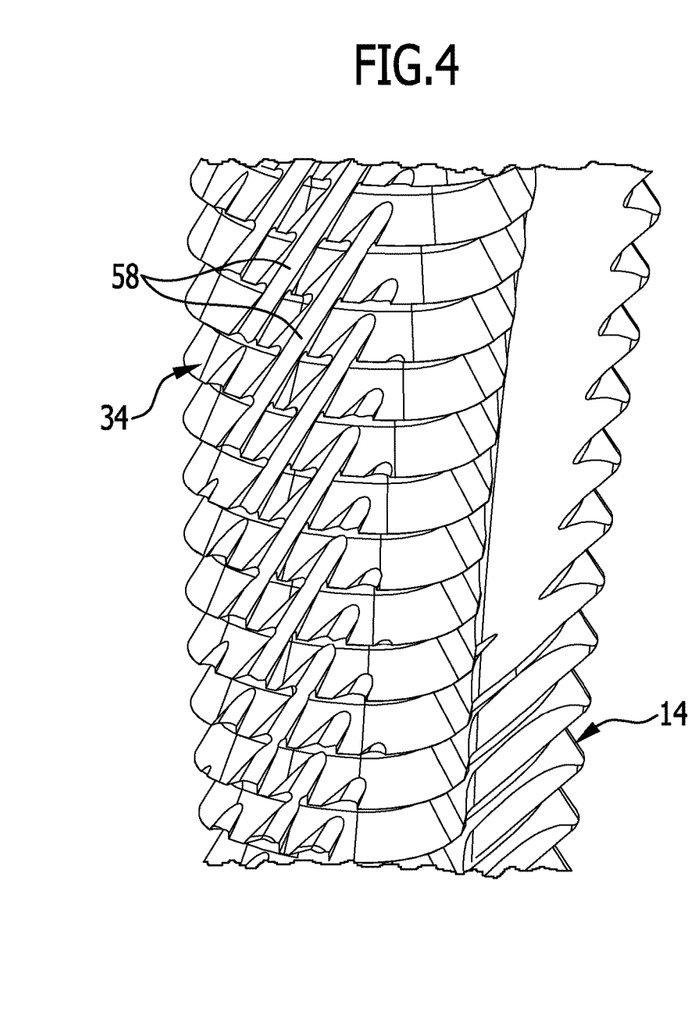
FIG. 4: shows an enlarged view of Region B in FIG. 2.
Figure 5:
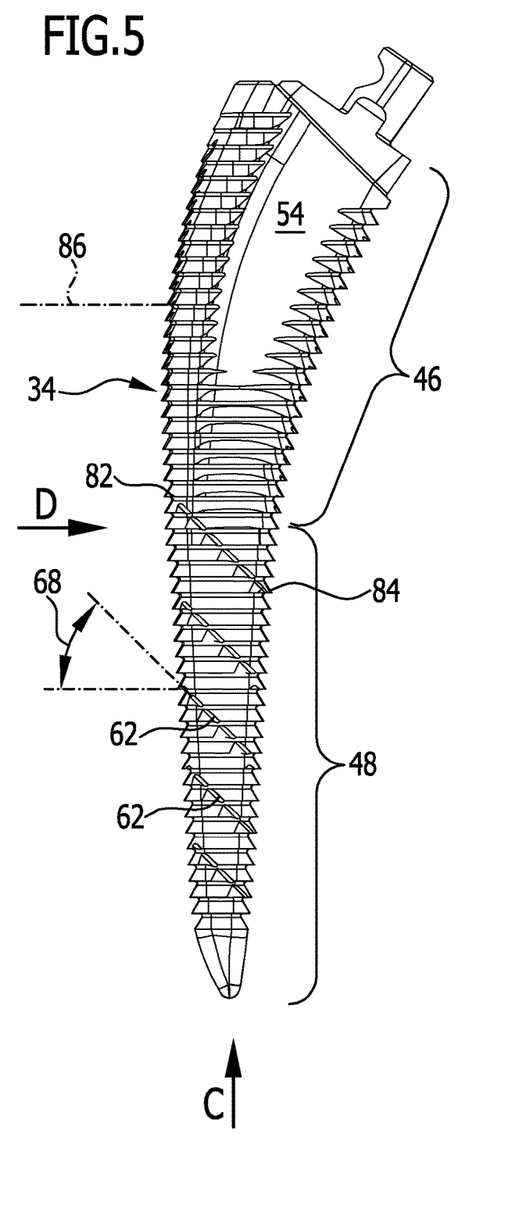
FIG. 5: shows a top view onto a posterior side face of the rasp shank from FIG. 1.
Figure 6:
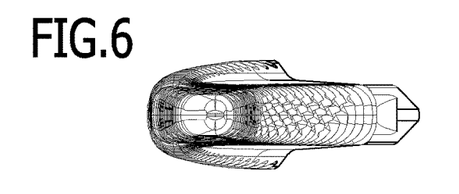
FIG. 6: shows a view of the rasp shank from FIG. 5 in the direction of Arrow C.
Figure 7:
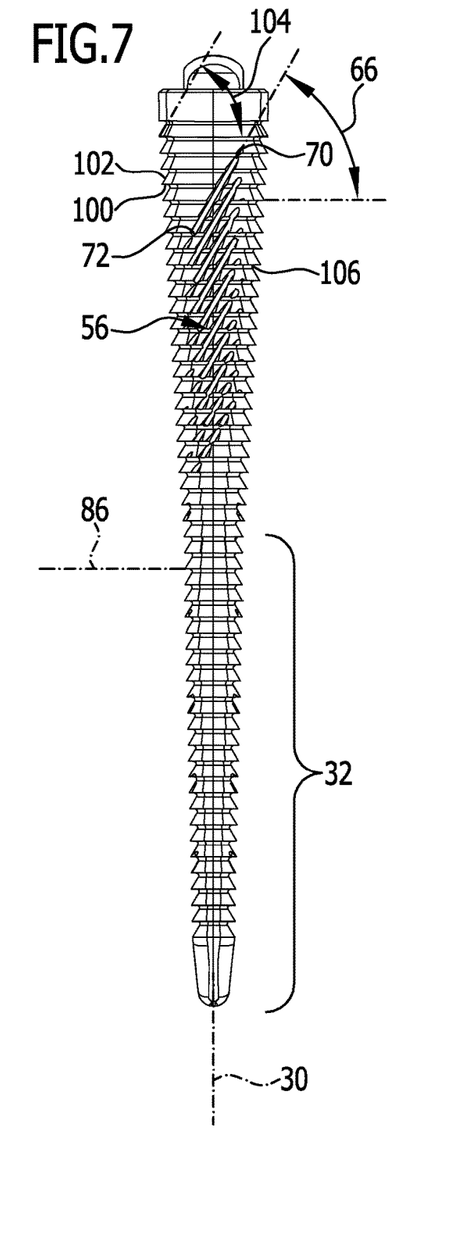
FIG. 7: shows a view of the rasp shank from FIG. 5 in the direction of Arrow D.
Figure 8:
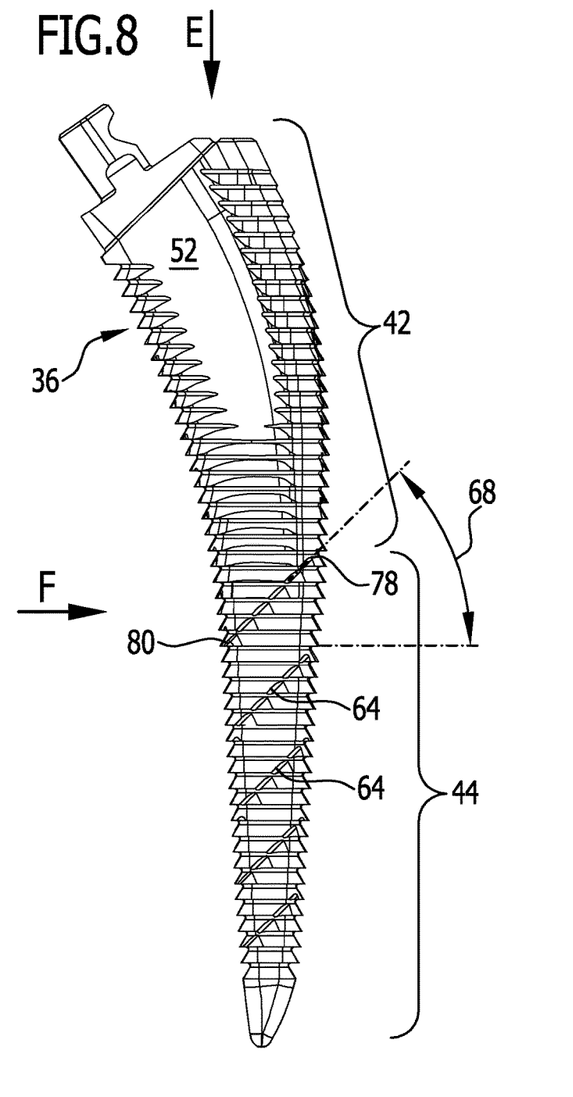
FIG. 8: shows a top view onto an anterior side face of the rasp shank from FIG. 1.
Figure 9:
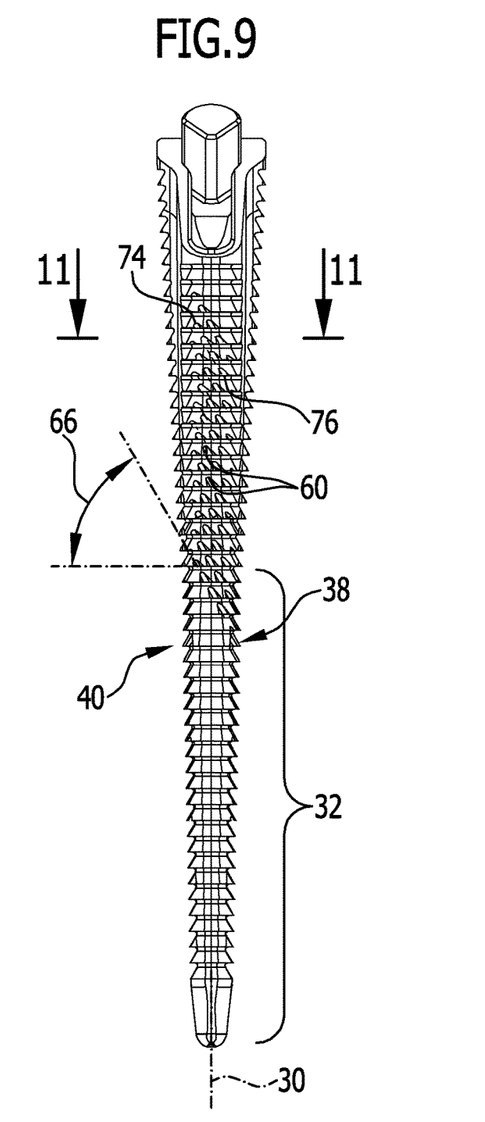
FIG. 9: shows a view of the rasp shank from FIG. 8 in the direction of Arrow F.
Figure 10:
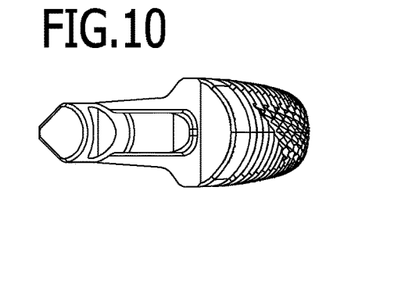
FIG. 10: shows a view of the rasp shank from FIG. 8 in the direction of Arrow E.

The rasp instrument 10 comprises a rasp shank 14 and optionally a rasp grip 16 schematically depicted in FIG. 2, which rasp grip in a coupling position is connected to the rasp shank 14 and in a cleaning position is disconnected therefrom.

A first coupling element 18 in the form of a non-round coupling pin 22 is formed sticking out from a proximal end face 20 of the rasp shank 14 for detachably connecting the rasp shank 14 and the rasp grip 16.

Formed on the rasp grip 16 is a second coupling element 24 which is engaged in a force- and/or form-locking manner with the first coupling element 18, such that the rasp shank 14 and the rasp grip 16 in the coupling position are connected to each other The second coupling element 24 is schematically depicted as a coupling receiver 26 in FIG. 2.

The first coupling element 18 and the second coupling element 24 form a coupling device of the rasp instrument 10 designated as a whole by the reference numeral 28.

The rasp shank 10 defines a longitudinal axis 30, namely with a distal end section 32 thereof.

The rasp shank has four side faces in total, namely a lateral side face 34, a medial side face 36, an anterior side face 38, and a posterior side face 40. The four stated side faces 34, 36, 38, and 40 merge in a substantially rounded manner. The lateral side face 34 has a proximal side face region 42 and a distal side face region 44. The proximal side face region 42 is convexly curved pointing away from the rasp shank 14 in a direction parallel to the longitudinal axis 30 and is also convexly curved pointing away from the rasp shank 14 in a direction perpendicular to the longitudinal axis. A doubly curved proximal side face region 42 is thus defined.

The medial side face 36 defines a proximal side face region 46 and a distal side face region 48. The proximal side face region 46 is concavely curved pointing away from the rasp shank 14 in a direction parallel to the longitudinal axis 30 and is planar or slightly convexly curved pointing away from the rasp shank in a direction perpendicular to the longitudinal axis 30.

On each of all four side faces 34, 36, 38, and 40, a multitude of rasp teeth 50 is formed which are formed running parallel to each other and circumferential or at least partially circumferential with respect to the longitudinal axis 30. Circumferential here means in particular that a self-contained rasp tooth extending around the rasp shank on all for side faces 34, 36, 38, 40 is formed.

The rasp teeth 50 may be partially interrupted, for example by a face region 52 of the anterior side face 38. Said region extends commencing from the end section 32 in distal direction, but not out over the proximal side face regions 42 and 46 in distal direction. A laterally-reversed shaped face region 54 free of stabilization grooves is formed on the posterior side face 40.

The particularity of the rasp shank 14 forms a rotational stabilization device designated as a whole by the reference numeral 56 for increasing a rotational stability of the rasp shank 14 driven into a bone cavity. In particular, the bone cavity may be a femur cavity.

The rotational stabilization device 56 comprises a multitude of stabilization grooves 58, 60, 62, and 64. The stabilization grooves 58 are formed on the lateral side face 34, the stabilization grooves 60 on the medial side face 36, the stabilization grooves 62 on the posterior side face 40, and the stabilization grooves 64 on the anterior side face 38.

The stabilization grooves 58 and 60 are each formed in the proximal side face regions 42 and 62, respectively.

The stabilization grooves 62 and 64 are each formed on the distal side of the proximal side face regions 42 and 46, that is, in distal side face regions of the posterior and anterior side faces 40 and 38.

The stabilization grooves 58, 60, 62, and 64 run obliquely to the rasp teeth 50, namely at identical stabilization angles 66 between the stabilization grooves 58 and the rasp teeth 50 and between the stabilization grooves 60 and the rasp tooth 50, respectively.

The stabilization grooves 68 are defined, on the one hand, between the rasp teeth 50 and the stabilization grooves 62 and between the rasp teeth 50 and the stabilization grooves 64 on the other.

The stabilization angles 66 and 68 are preferably in a range from about 30° to about 60°. In particular, they may be in a range from about 40° to about 50°. Ideally, the stabilization angle 66 is somewhat larger than the stabilization angle 68.

The stabilization grooves 58 formed on the lateral side face 34 have proximal stabilization groove ends 70 that are positioned closer to the posterior side face 40 than to the anterior side face 38.

In contrast, distal stabilization groove ends 72 of the stabilization grooves 58 are positioned closer to the anterior side face 38 than to the posterior side face 40. In addition, the proximal stabilization groove ends 70 are positioned further proximally with respect to the longitudinal axis 30 than the distal stabilization groove ends 72.

Moreover, proximal stabilization groove ends 74 of the stabilization grooves 60 formed on the medial side face 36 are positioned closer to the posterior side face 40 than to the anterior side face 38.

In contrast, distal stabilization groove ends 76 of the stabilization grooves 60 are positioned closer to the anterior side face 38 than to the posterior side face 40. In addition, the proximal stabilization groove ends 74, too, are positioned further proximally with respect to the longitudinal axis 30 than the distal stabilization groove ends 76.

Further, proximal stabilization groove ends 78 of the stabilization grooves 64 formed on the anterior side face 38 are positioned closer to the lateral side face 34 than to the medial side face 36.

In contrast, distal stabilization groove ends 80 of the stabilization grooves 64 are positioned closer to the medial side face 36 than to the lateral side face 34. In addition, the proximal stabilization groove ends 78 are positioned further proximally with respect to the longitudinal axis 30 than the distal stabilization groove ends 80.

Moreover, proximal stabilization groove ends 82 of the stabilization grooves 62 formed on the posterior side face 40 are positioned closer to the lateral side face 34 than to the medial side face 36.

Further, distal stabilization groove ends 84 of the stabilization grooves 62 are positioned closer to the medial side face 36 than to the lateral side face 34. In addition, the proximal stabilization groove ends are positioned further proximally with respect to the longitudinal axis 30 than the distal stabilization groove ends 84.

The circumferential or substantially circumferential rasp teeth 50 each define a rasp tooth plane 86 which run transversely, in the embodiment of the rasp shank 14 depicted for example in the Figures, perpendicularly to the longitudinal axis 30.

In particular the stabilization grooves 58 and 60, optionally also the stabilization grooves 62 and 64, at least partially have a U-shaped or V-shaped cross-sectional shape. This may be discerned in particular in FIG. 11.

Figure 11:
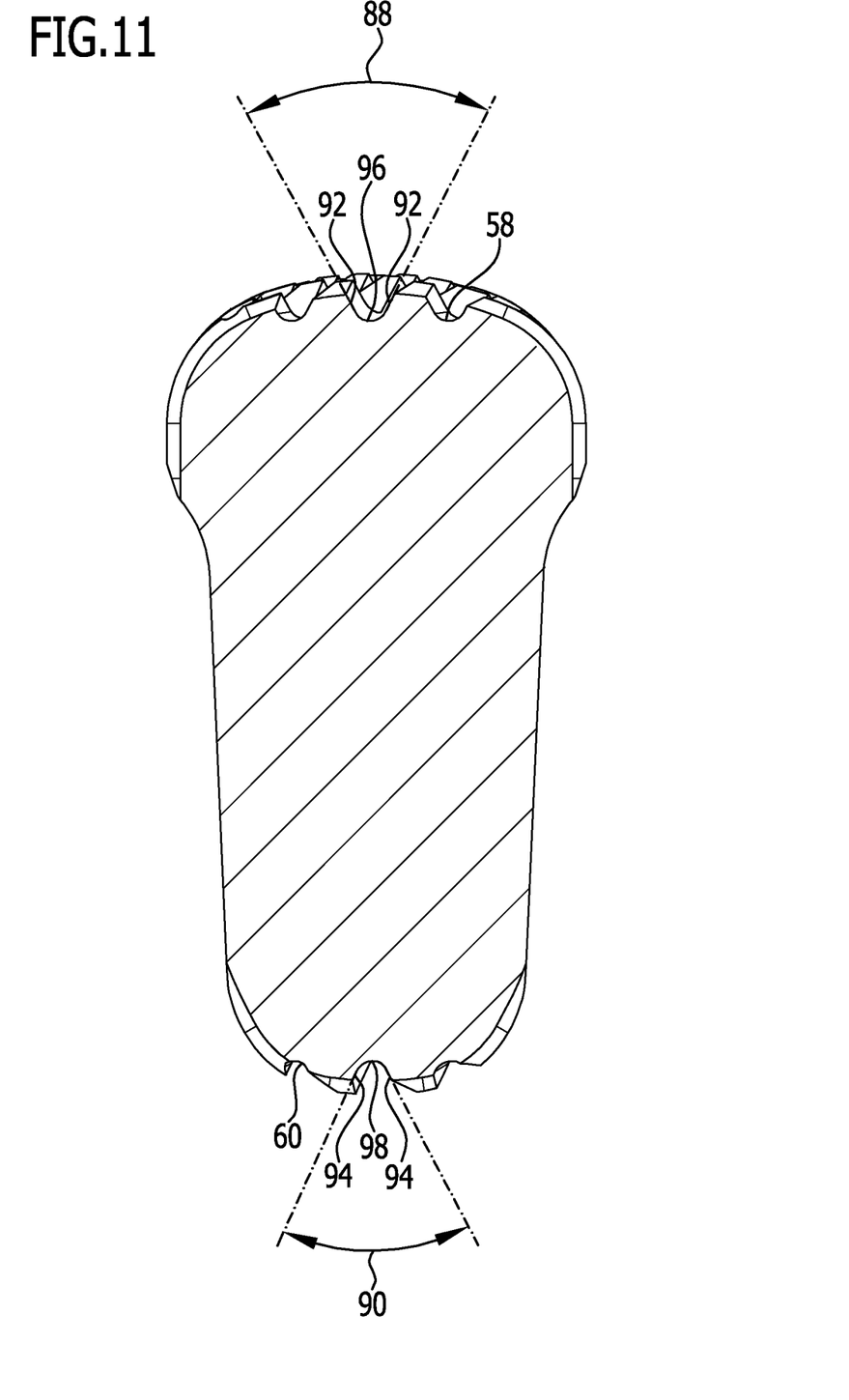
FIG. 11: shows a sectional view along Line 11-11 in FIG. 9.

The V-shaped cross-sectional shape schematically depicted in FIG. 11 defines a groove opening angle 88 between groove side faces 92 of the stabilization grooves 58 tilted relative to each other.

Likewise, groove side faces 94 of the stabilization grooves 60 tilted relative to each other define between them a groove opening angle 90. The groove opening angles 88 and 90 are preferably in a range from about 30° to about 60°. In particular, they are in a range from about 40° to about 50°.

The stabilization grooves 58, 60, 62, and 64 each have a rounded groove base 96 and 98, respectively.

A groove depth of the stabilization grooves 58 on the lateral side face 34 is preferably greater than a tooth depth of the rasp teeth 50. Further, a groove depth of the stabilization grooves 60 on the medial side face 36 is preferably less than a tooth depth of the rasp teeth 50.

Moreover, a groove depth of the stabilization grooves 62 and 64 on the anterior side face 38 and/or on the posterior side face 40 is less than a tooth depth of the rasp teeth 50.

Figure 1:
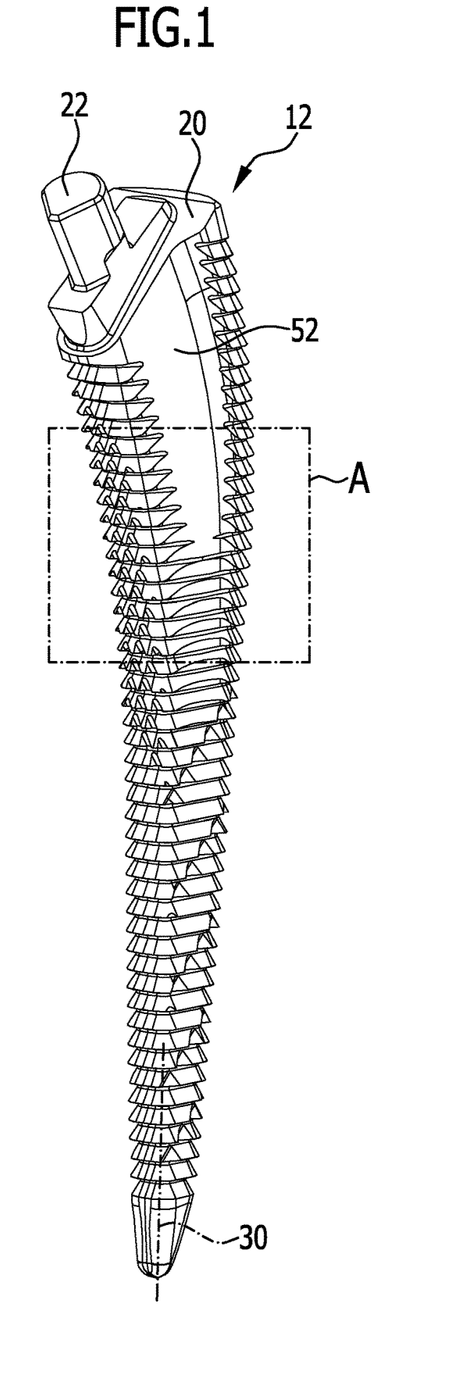
FIG. 1: shows a perspective view of a rasp shank in the direction toward its medial side face and anterior side face.

As may be discerned in FIGS. 1 and 2, the stabilization grooves 60 of the medial side face 36 are formed in the proximal or substantially in the proximal side face region 46 of the medial side face 36. In contrast, the stabilization grooves 58 of the lateral side face 34 are formed in the proximal or substantially in the proximal side face region 42 of the lateral side face 34.

The anterior side face 38, the posterior side face 40, and the lateral side face 34, as well as the medial side face 36 are formed at least partially planar or substantially planar. In particular, this applies to the distal side face regions 44 and 48 of all four side faces 34, 36, 38, and 40.

The stabilization grooves 62 and 64 of the anterior side face 38 and of the posterior side face 40 are preferably formed on the distal side of the proximal side face regions 42 and 46 of the lateral side face 34 and of the medial side face 36.

The rasp teeth 50 have a first rasp tooth side face 100 that runs transversely or substantially transversely to the longitudinal axis 30 and points in distal direction. Further, the rasp teeth 50 have a second rasp tooth side face 102 that is tilted with respect to the longitudinal axis and points substantially in proximal direction.

The first and second rasp tooth side faces 100 and 102 define between them a rasp tooth angle 104. This is preferably less than 90°, in particular less than 70°.

Further, the first rasp tooth side face 100 may be tilted pointing somewhat in the direction toward the longitudinal axis 30 for forming of an undercut 106 acting in distal direction.

The rasp shank 14 is preferably integrally formed and manufactured out of a solid material by machining.

The medical instrumentarium 12 may in particular comprise multiple rasp shanks 14 of various sizes, with which the bone cavity may successively be processed, namely beginning with the smallest rasp shank 14. Successively larger rasp shanks 14 are driven into the bone cavity until the rasp shank 14 lastly driven in is positioned in the bone cavity how the surgeon would like to position the implant stem that is to be permanently implanted.

The rasp shank 16 is preferably coupleable to all rasp shanks 14 of the medical instrumentarium.

REFERENCE NUMERAL LIST 10 rasp instrument
12 instrumentarium
14 rasp shank
16 rasp grip
18 first coupling element
20 end face
22 coupling pin
24 second coupling element
26 coupling receiver
28 coupling device
30 longitudinal axis
32 end section
34 lateral side face
36 medial side face
38 anterior side face
40 posterior side face
42 proximal side face region
44 distal side face region
46 proximal side face region
48 distal side face region
50 rasp tooth
52 face region
54 face region
56 rotational stabilization device
58 stabilization groove
60 stabilization groove
62 stabilization groove
64 stabilization groove
66 stabilization angle
68 stabilization angle
70 proximal stabilization groove end
72 distal stabilization groove end
74 proximal stabilization groove end
76 distal stabilization groove end
78 proximal stabilization groove end
80 distal stabilization groove end
82 proximal stabilization groove end
84 distal stabilization groove end
86 rasp tooth plane
88 groove opening angle
90 groove opening angle
92 groove side face
94 groove side face
96 groove base
98 groove base
100 first rasp tooth side face
102 second rasp tooth side face
104 rasp tooth angle
106 undercut

What is claimed is:

1. A medical instrumentarium for implanting a hip joint stem, comprising: a rasp instrument with a rasp shank defining a longitudinal axis, which rasp shank has an anterior side face, a posterior side face, a medial side face, and a lateral side face, wherein the side faces at least partially have rasp teeth which are formed running parallel to each other and circumferential or at least partially circumferential with respect to the longitudinal axis, wherein the rasp instrument comprises a rotational stabilization device for increasing a rotational stability of the rasp shank driven into a bone cavity, in particular a femur cavity; wherein the rotational stabilization device comprises a multitude of stabilization grooves on at least one side face of the rasp shank and wherein the multitude of stabilization grooves runs obliquely relative to the rasp teeth; wherein the multitude of stabilization grooves is formed at least one of on the lateral side face and on the medial side face and on the anterior side face and on the posterior side face of the rasp shank; wherein the multitude of stabilization grooves that are formed on the lateral side face and on the medial side face all run parallel or substantially parallel to each other.

2. The medical instrumentarium according to claim 1, wherein the multitude of stabilization grooves running obliquely relative to the rasp teeth run at a stabilization angle in a range from about 30° to about 60°, in particular in a range from about 40° to about 50°.

3. The medical instrumentarium according to claim 1, wherein at least one of:
    a) the multitude of stabilization grooves that are formed on the anterior side face and on the posterior side face all run parallel or substantially parallel to each other; and
    b) proximal stabilization groove ends of the stabilization grooves formed on the lateral side face are positioned closer to the posterior side face than to the anterior side face, and distal stabilization groove ends of the stabilization grooves formed on the lateral side face are positioned closer to the anterior side face than to the posterior side face, and the proximal stabilization grooves are positioned further proximally with respect to the longitudinal axis than the distal stabilization groove ends; and c) proximal stabilization groove ends of the stabilization grooves formed on the medial side face are positioned closer to the posterior side face than to the anterior side face, and distal stabilization groove ends of the stabilization grooves formed on the medial side face are positioned closer to the anterior side face than to the posterior side face, and the proximal stabilization groove ends are positioned further proximally with respect to the longitudinal axis than the distal stabilization groove ends; and d) proximal stabilization groove ends of the stabilization grooves formed on the anterior side face are positioned closer to the lateral side face than to the medial side face, and distal stabilization groove ends of the stabilization grooves formed on the anterior side face are positioned closer to the medial side face than to the lateral side face, and the proximal stabilization groove ends are positioned further proximally with respect to the longitudinal axis than the distal stabilization groove ends; and e) proximal stabilization groove ends of the stabilization grooves formed on the posterior side face are positioned closer to the lateral side face than to the medial side face, and distal stabilization groove ends of the stabilization grooves formed on the posterior side face are positioned closer to the medial side face than to the lateral side face, and the proximal stabilization groove ends are positioned further proximally with respect to the longitudinal axis than the distal stabilization groove ends; and f) the circumferential or substantially circumferential rasp teeth each define a rasp tooth plane which runs transversely, in particular perpendicularly, to the longitudinal axis.

4. The medical instrumentarium according to claim 1, wherein the multitude of stabilization grooves at least partially has a U-shaped or V-shaped cross-sectional shape; and
   wherein in particular the V-shaped cross-sectional shape defines a groove opening angle between groove side faces of a stabilization groove tilted relative to each other, which is in a range from about 30° to about 60°, in particular in a range from about 40° to about 50°.

5. The medical instrumentarium according to claim 1, wherein at least one of:
   a) the multitude of stabilization grooves has a chamfered groove base; and
   b) a groove depth of the multitude of stabilization grooves on the lateral side face is greater than a tooth depth of the rasp teeth; and c) a groove depth of the multitude of stabilization grooves on the medial side face is less than a tooth depth of the rasp teeth; and
   d) a groove depth of the multitude of stabilization grooves at least one of on the anterior side face and on the posterior side face is less than a tooth depth of the rasp teeth.

6. The medical instrumentarium according to claim 1, wherein the medial side face has a proximal side face region and a distal side face region, and wherein the proximal side face region is concavely curved pointing away from the rasp shank in a direction parallel to the longitudinal axis and is planar or convexly curved pointing away from the rasp shank in a direction perpendicular to the longitudinal axis, and
   wherein in particular the multitude of stabilization grooves of the medial side face is formed in the proximal or substantially in the proximal side face region.

7. The medical instrumentarium according to claim 1, wherein the lateral side face has a proximal side face region and a distal side face region, and wherein the proximal side face region is convexly curved pointing away from the rasp shank in a direction parallel to the longitudinal axis and is planar or convexly curved pointing away from the rasp shank in a direction perpendicular to the longitudinal axis.

8. The medical instrumentarium according to claim 7, wherein the multitude of stabilization grooves of the lateral side face is formed in the proximal or substantially in the proximal side face region.

9. The medical instrumentarium according to claim 6, wherein the multitude of stabilization grooves of at least one of the anterior side face and the posterior side face are formed on the distal side of the proximal side face regions of at least one of the lateral side face and the medial side face.

10. The medical instrumentarium according to claim 1, wherein the rasp teeth have a first rasp tooth side face running transversely or substantially transversely to the longitudinal axis and pointing in distal direction and a second rasp tooth side face tilted with respect to the longitudinal axis and pointing substantially in proximal direction.

11. The medical instrumentarium according to claim 10, wherein at least one of:
    a) the first and second rasp tooth side faces define between them a rasp tooth angle which is less than 90°, in particular less than 70°, and
    b) the first rasp tooth side face is tilted pointing somewhat in the direction toward the longitudinal axis for forming an undercut effective in the distal direction.

12. The medical instrumentarium according to claim 1, wherein the rasp shank comprises a distal end section, and wherein the distal end section of the rasp shank defines the longitudinal axis.

13. The medical instrumentarium according to a claim 1, wherein at least one of the anterior side face and the posterior side face and the lateral side face and the medial side face are formed at least partially planar or substantially planar.

14. The medical instrumentarium according to claim 1, wherein a first coupling element is arranged or formed on the rasp shank in the region of its proximal end for detachably connecting to a rasp grip.

15. The medical instrumentarium according to claim 1, wherein the rasp instrument is modularly formed and comprises a rasp grip that is detachably connectable to the rasp shank,
    wherein in particular the rasp grip comprises a second coupling element which, in a coupling position, is engaged with the first coupling element and, in a cleaning position, is disengaged.

16. A medical instrumentarium, in particular for implanting a hip joint stem, comprising a rasp instrument with a rasp shank defining a longitudinal axis, which rasp shank has an anterior side face, a posterior side face, a medial side face, and a lateral side face, wherein the side faces at least partially have rasp teeth which are formed running parallel to each other and circumferential or at least partially circumferential with respect to the longitudinal axis, wherein the rasp instrument comprises a rotational stabilization device for increasing a rotational stability of the rasp shank driven into a bone cavity, in particular a femur cavity, wherein the rotational stabilization device comprises a multitude of stabilization grooves on at least one side face of the rasp shank and wherein the multitude of stabilization grooves runs obliquely relative to the rasp teeth, wherein the multitude of stabilization grooves at least partially has a U-shaped or V-shaped cross-sectional shape, wherein a groove depth of the multitude of stabilization grooves on the lateral side face is greater than a tooth depth of the rasp teeth, and wherein a groove depth of the multitude of stabilization grooves on the medial side face is less than a tooth depth of the rasp teeth.

17. A medical instrumentarium for implanting a hip joint stem, comprising: a rasp instrument with a rasp shank defining a longitudinal axis, which rasp shank has an anterior side face, a posterior side face, a medial side face, and a lateral side face, wherein the side faces at least partially have rasp teeth which are formed running parallel to each other and circumferential or at least partially circumferential with respect to the longitudinal axis, wherein the rasp instrument comprises a rotational stabilization device for increasing a rotational stability of the rasp shank driven into a bone cavity, in particular a femur cavity, wherein the rotational stabilization device comprises a multitude of stabilization grooves on at least one side face of the rasp shank and wherein the multitude of stabilization grooves runs obliquely relative to the rasp teeth, wherein the medial side face has a proximal side face region and a distal side face region, and wherein the proximal side face region is concavely curved pointing away from the rasp shank in a direction parallel to the longitudinal axis and is planar or convexly curved pointing away from the rasp shank in a direction perpendicular to the longitudinal axis, and wherein the multitude of stabilization grooves of the medial side face is formed in the proximal or substantially in the proximal side face region; wherein the rotational stabilization device comprises a multitude of stabilization grooves on at least one side face of the rasp shank and wherein the multitude of stabilization grooves formed at least one of on the lateral side face and on the medial side face and on the anterior side face and on the posterior side face of the rasp shank; wherein the multitude of stabilization grooves that are formed on the lateral side face and on the medial side face all run parallel or substantially parallel to each other.

* * * * *

UNITED STATES PATENT AND TRADEMARK OFFICE
CERTIFICATE OF CORRECTION

PATENT NO. : 10,702,286 B2
APPLICATION NO. : 16/016834
DATED : July 7, 2020
INVENTOR(S) : Hirt et al.

Page 1 of 1

It is certified that error appears in the above-identified patent and that said Letters Patent is hereby corrected as shown below:

In the Claims

Column 16, Line 14 In Claim 17:
"stabilization grooves formed at least one of on the lateral"

Should read:
-- stabilization grooves runs obliquely relative to the rasp teeth; wherein the multitude of stabilization grooves is formed at least one of on the lateral --

Signed and Sealed this
Third Day of November, 2020

Andrei Iancu
*Director of the United States Patent and Trademark Office*